United States Patent [19]
Jette

[11] Patent Number: 5,416,406
[45] Date of Patent: May 16, 1995

[54] ELECTRIC CHARGE METERING DEVICE AND METHOD

[75] Inventor: Bruce D. Jette, Eatontown, N.J.

[73] Assignee: The United States of America as represented by the Secretary of the Army, Washington, D.C.

[21] Appl. No.: 81,594

[22] Filed: Jun. 23, 1993

Related U.S. Application Data

[63] Continuation-in-part of Ser. No. 820,835, Sep. 15, 1992, abandoned.

[51] Int. Cl.$^6$ .................. G01R 27/22; G01N 27/07
[52] U.S. Cl. .................. 324/94; 324/439; 320/48
[58] Field of Search ......... 324/426, 427, 428, 439, 324/94; 320/48; 340/636

[56] References Cited

U.S. PATENT DOCUMENTS

| | | | |
|---|---|---|---|
| 3,302,091 | 1/1967 | Henderson | 324/94 X |
| 3,638,120 | 1/1972 | Jost | 324/94 X |
| 4,015,150 | 3/1977 | Jones | 324/94 X |
| 4,100,490 | 7/1978 | Peck et al. | 324/94 X |
| 4,164,004 | 8/1979 | Saito | 324/94 X |

Primary Examiner—Kenneth A. Wieder
Assistant Examiner—Diep Do
Attorney, Agent, or Firm—Michael Zelenka; William H. Anderson

[57] ABSTRACT

An electrochemical cell includes a metallic anode electrode and a metallic cathode electrode substantially immersed in an electrolyte. As charge or current is passed through the cell from the anode electrode to the cathode electrode, the anode electrode is consumed and the cathode electrode plated, causing the resistance therebetween to change. The change in resistance provides a measure f or both the total charge passed through the cell over an interval of time, and for the total time charge flowed through the cell over an interval of time between resistance measurements.

19 Claims, 5 Drawing Sheets

ELECTRIC CHARGE METERING DEVICE AND METHOD

GOVERNMENT INTEREST

The invention described herein may be manufactured, used, and licensed by, or on behalf of, the Government of the United States of America without the payment to me of any royalty thereon.

CONTINUATION IN PART

The present application is a continuation in part of U.S. Ser. No. 07/820,835, filed Jan. 15, 1992 by the inventor herein and entitled, "Electrochemical Coulometer and Method," now abandoned. Priority of U.S. Ser. No. 07/820,835 is claimed.

FIELD OF THE INVENTION

The field of the present invention relates generally to ammeters, and more particularly to devices for measuring and indicating the number of coulombs of electric charge passed through a circuit over an interval of time.

BACKGROUND OF THE INVENTION

A number of batteries in wide-spread use in the U.S. Armed Forces and industry do not exhibit a voltage drop prior to discharge to a useless level. Instead they exhibit constant voltage until nearly all the charge in the battery is exhausted; then, the voltage drops rapidly and no further power is produced. The life of such a battery cannot be determined by conventional techniques such as voltage measurements. Lithium batteries such as those used in man-pack radios are an example of such a battery. Because the life or failure point of such batteries cannot be easily determined, soldiers will often replace batteries with significant lifetimes remaining rather than chance their failure in the field. This wastes batteries causing the Army to purchase large numbers of excess replacements. These discarded batteries are considered hazardous waste because they have not been fully discharged.

A given battery design provides a fixed number of coulombs during its useful lifetime; therefore, batteries which exhibit this type of behavior could be tested if a circuit could be attached which would determine the number of coulombs passed. Known electronic circuits perform this task either capacitively or digitally. The former has a tendency to leak the charge stored causing inaccurate readings over long periods of time, while the latter is cost prohibitive.

In other applications unrelated to batteries specifically, but generally related to electrical systems where an indication of actual total time of operation is required, coulomb measuring devices may be useful. For example, the running time of an aircraft engine, truck engine, rental car engine, or other electrically related devices may be of interest for maintenance scheduling, and so forth.

To date, no cost effective device has been produced which could provide a coulometric monitoring of a battery, power source, or other current source. Such a device could provide an indication of a certain coulomb limit, a series of coulomb limits, or continuous status of coulombs passed in constant voltage batteries such as lithium batteries.

SUMMARY OF THE INVENTION

In one embodiment, the invention consists of a thin film of inexpensive metal such as copper deposited on an inexpensive non-conductor, such as polyethylene to form the anode, and similarly to form the cathode. Electrolyte solution is provided by thin pads of material or structure such as woven fabric which is saturated with the electrolyte. Indications of charge remaining can be provided by LED meters. As current passes through this electrochemical cell, the anode is consumed through oxidation of the metal and the resultant metal ions are then plated at the cathode. Since the anode is consumed, the anode surface area is reduced thereby altering the over all resistivity of the electrochemical cell. The change in resistivity can then be measured in a conventional manner and from this change in resistivity, the number of coulombs passing through the electrochemical cell can be measured.

The invention may be used to indicate total charge or current consumed over a period of time for any number of purposes. For example, connection of the invention to a constant current source would allow use of the device as a timer or the device may measure the charge passing from a battery to an application. As a timer, the anode would be dissolved into solution after a specific number of coulombs passed which would cause some action after a quantity of current has passed or a predetermined period of operation has passed, could be monitored by this device. An example would be a missile which should self destruct after no target is encountered and the battery is depleted. Further, a circuit may be included in the device and connected to a battery such that after a specific number of coulombs have passed through the device the battery is completely discharged. This would convert the chemicals comprising the battery to lithium salts reducing it from a hazardous waste product to a disposable item.

As indicated above, another application of the invention provides for monitoring any current driven system. An example of such a system is monitoring the operational hours of an avionics package in an aircraft. An embodiment of the present device is connected in parallel to the primary source of current for the avionics package in the same manner as for monitoring a battery. As the avionics package is used, the present device detects the amount of current passing through the avionics package in the same way as it detects the passing of current out of a battery.

If the specific chemistry of the present device is selected so the electrochemical depletion of the anode is not reversible, the device becomes an irreversible monitor of usage of the system. If the specific chemistry of the present device is selected so the electrochemical depletion of the anode is reversible, the device becomes a reversible monitor of usage of the system and allows for reverse current flow of the system to reset the electrode and the resulting device indication.

For measuring the coulombs which pass through a given circuit, the inventive device may be placed in series with the circuit to be monitored. As current passes through the inventive device, it is resistively divided to permit a desired portion of the net current to pass through an electrochemical cell. The cell consists of two plates of common or dissimilar metals separated by an electrolytic solution. Current passing through the cell causes the ions in solution to plate out by reduction at the cathode, while some of the anode is consumed by oxidation while replenishing the electrolyte. Because the electrolyte concentration is maintained, the solution resistance remains constant until the anode surface begins to decrease due to oxidation. The resulting change in resistance can then be measured by an included detection circuit which operates continuously or periodically to determine the change in resistivity of the cell. Therefore, an indication can be provided as to the amount of coulombs passed or a desired automatic action taken.

BRIEF DESCRIPTION OF THE DRAWINGS

Various embodiments of the invention are described in detail below with reference to the following drawings, in which like items are indicated by the same reference designation, wherein.

DETAILED DESCRIPTION

Figure 1:
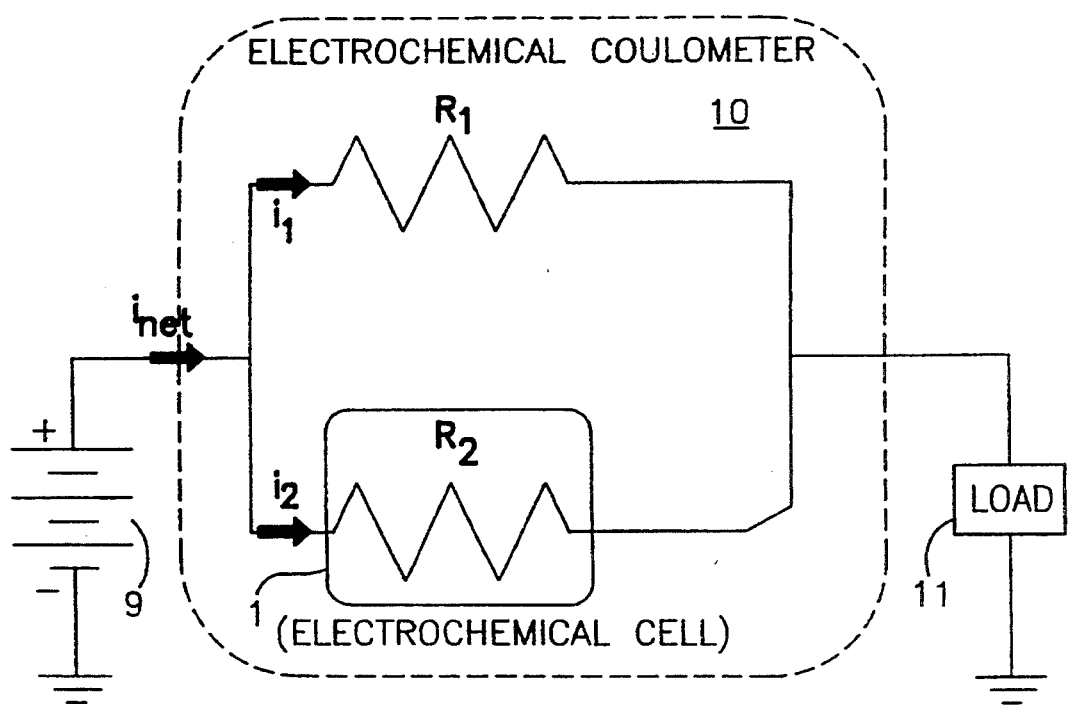
FIG. 1 is a simplistic circuit schematic diagram showing one embodiment of the invention.

FIG. 1 illustrates one example of the present invention which generically comprises a resistive network, electrochemical cell connected within the resistive network and a measuring circuit.

As shown in FIG. 1, the resistive network consists of two resistors $R_1$ and $R_2$ connected in parallel. The resistance $R_2$ of electrochemical cell 1 is used to measure coulombs. The other resistor $R_1$ has a resistance value relative to $R_2$ for permitting a desired proportion of the net current ($i_{net}$) to pass through the electrochemical cell 1.

Figure 2:
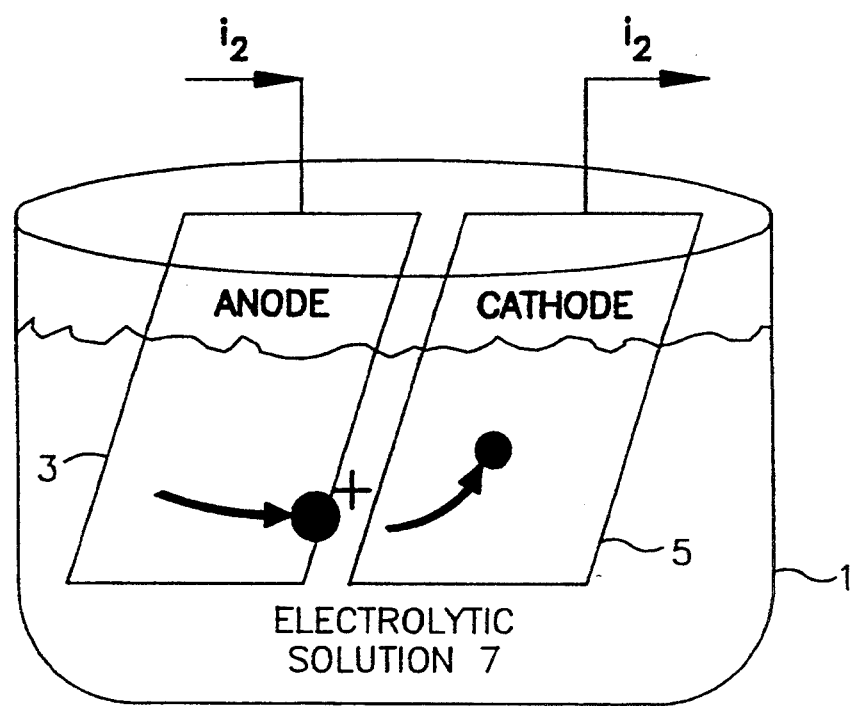
FIG. 2 is a simplified pictorial diagram showing an electrochemical cell of an embodiment of the invention.

As shown in FIG. 2, the electrochemical cell 1 consists of anode and cathode electrodes 3 and 5, respectively, in mutual contact with an electrolytic solution 7. The electrodes 3, 5 need not consist of the same metals. The electrolyte 7 is an electrolyte solution consisting of a concentration of metal salts, that can be aqueous or non-aqueous; or a combination of the two in liquid, solid or gel phase. During operation, the metal ions will be reduced at the cathode 5 (plated thereon), while the solution 7 is replenished with metal ions by oxidation of the anode 3 (dissolution). Metal ions originally in solution need not be the same as the metal of the anode 3.

The measuring circuit can consist of any a number of common measuring devices which will respond to a change in a detected voltage, current, or resistance. As the resistance of $R_2$ in the electrochemical cell 1 changes, the measuring circuit serves to detect such resistance changes by direct resistance measurement, measurement of a change in current or measurement of a change in voltage, and either provides some indication of the changes or takes some desired action.

It is important to note that the present device 10 need not consist of all three of the above components. For example, by eliminating the resistive network or resistor $R_1$, all current $i_{net}$ would pass through the resistance $R_2$ of electrochemical cell 1. Each coulomb of charge is counted, rather than a ratio thereof when shunt resistance $R_1$ is included. The measuring circuit could be eliminated as a component of the basic device and an external one applied to determine the status of the count.

FIG. 1 shows the inventive device 10 in series with a current source, in this example a battery 9, and a load 11. As indicated above, the invention can be modeled as two parallel resistors: $R_1$, the fixed resistance, and $R_2$, the electrochemical cell 1 resistance. These resistances $R_1$ and $R_2$ divide the net current $i_{net}$ into respective currents, $i_1$ and $i_2$. It is possible to establish a relationship between $i_{net}$ and $i_2$ through selection of the resistances. This relationship is determined by:

$$i_2 = i_{net} \frac{R_1}{(R_1 + R_2)}$$

The current, $i_2$, passes through the electrochemical cell 1 consisting of two metallic electrodes 3 and 5 in a solution 7. FIG. 2 shows the construction of the cell 1 diagrammatically and identifies the cathode 5 (working electrode), anode 3, and solution 7. In one configuration of the cell 1, both electrodes 3, 5 are comprised of the same metals. The solution 7 is initially of a set concentration of a metal salt in a solvent with or without supporting electrolyte. In the case of common metal electrodes, no potential is electrochemically established between the anode 3 and cathode 5. Assuming a large volume of electrolyte 7, the cell $R_2$ resistance may be modeled as the solution resistance to first approximation. This resistance is expressed as:

$$\frac{1}{R} = G = K \frac{a}{l}$$

where
R=Resistivity of the electrochemical cell 1
G=Conductivity of the electrochemical cell 1
K=Electrochemical conductivity of the solution 7
a=area of the anode electrode 3
l=distance separating the two electrodes 3 and 5

Using the definition of the electrochemical conductivity of solution:

$$K = \frac{C^*}{1000} (\lambda_+ + \lambda_-)$$

where
$C^*$ =Solution concentration (Normal)
$\lambda_\pm$ =Ionic conductance of the $\pm$ions Therefore the resistance $R_2$ of the electrochemical cell 1 is:

$$R_2 = \frac{1000}{C^*(\lambda_+ + \lambda_-)} \frac{1}{a}$$

As $i_2$ passes through the electrochemical cell 1, metal ions are electrodeposited (reduced) at the cathode 5. This would decrease the solution concentration except for the dissolution (oxidation) of the anode 3. This process continues at a constant resistance as long as current $i_2$ passes through cell 1, and until the surface area of the anode 3 begins to change. Equation (4) shows the dependance of the resistivity of the electrochemical cell on anode area a. It is this change in resistance of $R_2$ of the electrochemical cell 1 which is used to indicate the passage of a number of coulombs therethrough.

The first equation establishes the relationship between the net amount of charge passed through the present system 10 and the amount of charge passed through the electrochemical cell 1, since $$Q = N(n\mathcal{F})$$

where
 Q = Coulombs
 N = Moles electrolyzed
 n = Charge equivalence for the reaction
 $\mathcal{F}$ = Faraday's constant (coulombs per mole).

Therefore by substituting this last equation into the first and fourth equations for $R_2$ and including an efficiency factor, $\gamma$, a relationship is arrived at between the number of moles of the battery 9 consumed and the number of moles of the anode consumed:

$$N_a = N_b \frac{n_b}{n_a} \frac{R_1}{R_1 + \left(\frac{1000}{C^*(\lambda_+ \lambda_-)} \frac{1}{a}\right)} \gamma$$

where for those variables not defined above are
 $N_a$ = Number of moles of anode 3 consumed
 $N_b$ = Number of moles of battery consumed
 $n_a$ = Charge equivalence for the anode reaction
 $n_b$ = Charge equivalence for the battery reaction Since there is a direct relationship between the density of the soles, density, and surface area of the anode 3, this sixth equation can be expressed as a thickness of the anode 3:

$$T = \frac{A_{wt}}{\rho_2} N_b \frac{n_b}{n_a} \frac{1}{a} \frac{R_1}{R_1 + \left(\frac{1000}{C^*(\lambda_+ \lambda_-)} \frac{1}{a}\right)} \gamma$$

where for those variables not defined above
 $A_{wt}$ = Atomic weight of the anode 3 material
 $\rho$ = Density of the anode 3 material This seventh equation shows that for a specific number of moles of the battery 9 consumed an anode 3 of surface area, a, will be fully consumed to a thickness, T. Note this assumes no loss in electrical conductivity of the anode 3 through full oxidation. As the area of the anode 3 is so decreased, the fourth equation shows that the resistance will increase rapidly. This change in resistance of $R_2$ can be measured in various ways by an integral or separate measuring circuit.

Figure 3:
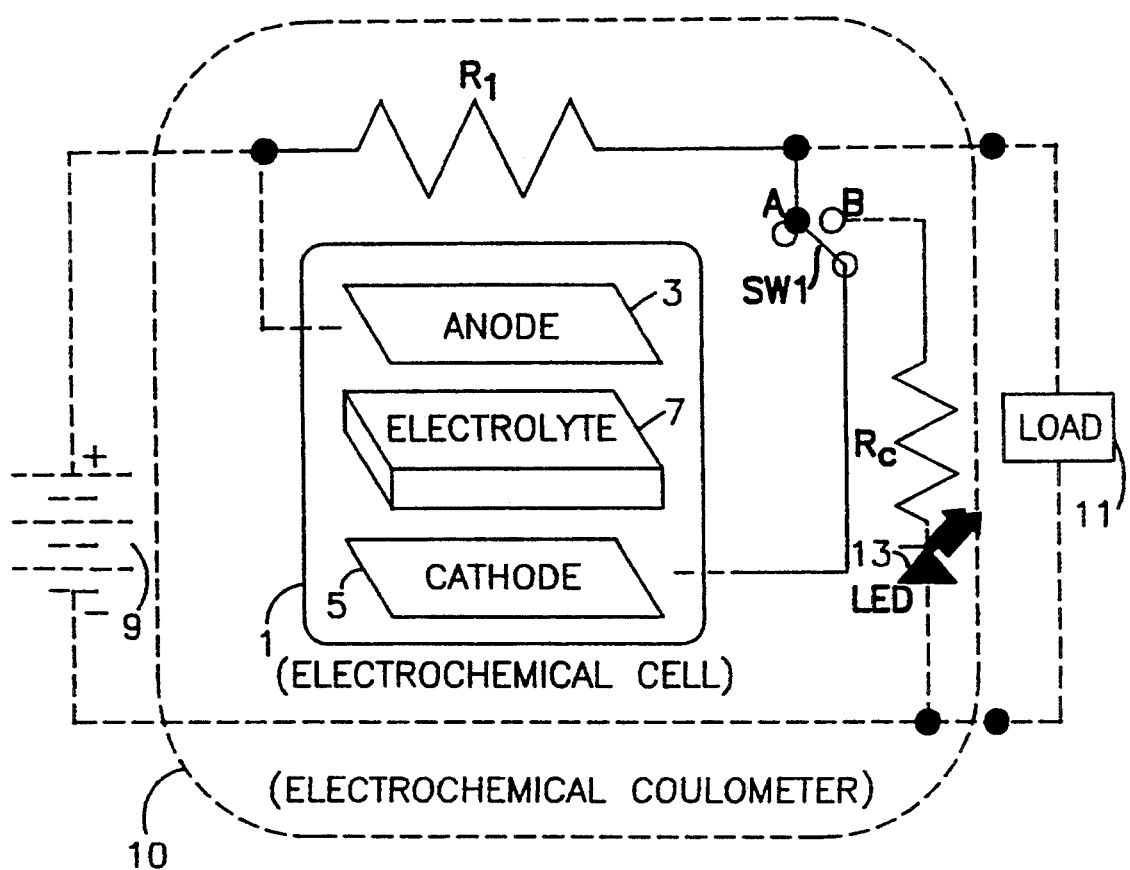
FIG. 3 is a partial pictorial and partial circuit schematic diagram of an embodiment of the invention.

FIG. 3 shows a complete diagram of one embodiment of the invention including a measuring device or circuit consisting of a resistor $R_c$ to limit the magnitude of current flowing through an LED meter 13, and a switch SW1. Normal operation occurs with the test switch SW1 in position A, whereby no current flows through $R_c$ and LED meter 13, but does flow from battery 9, through coulometer 10($R_1$ and electrochemical cell 1) to load 11. The resistance $R_2$ of electrochemical cell 1 is tested with the switch in position B, whereby current flows between battery 9, and the series circuit of electrochemical cell 1, resistor $R_c$, and LED meter 13, whereby the magnitude of light emitted by LED meter 13 is directly related to the value resistance $R_2$ of cell 1. The LED meter 13 lights if a threshold current is reached. If $R_1$ is too great, the LED meter 13 will not light indicating the battery has been consumed.

Figure 4:
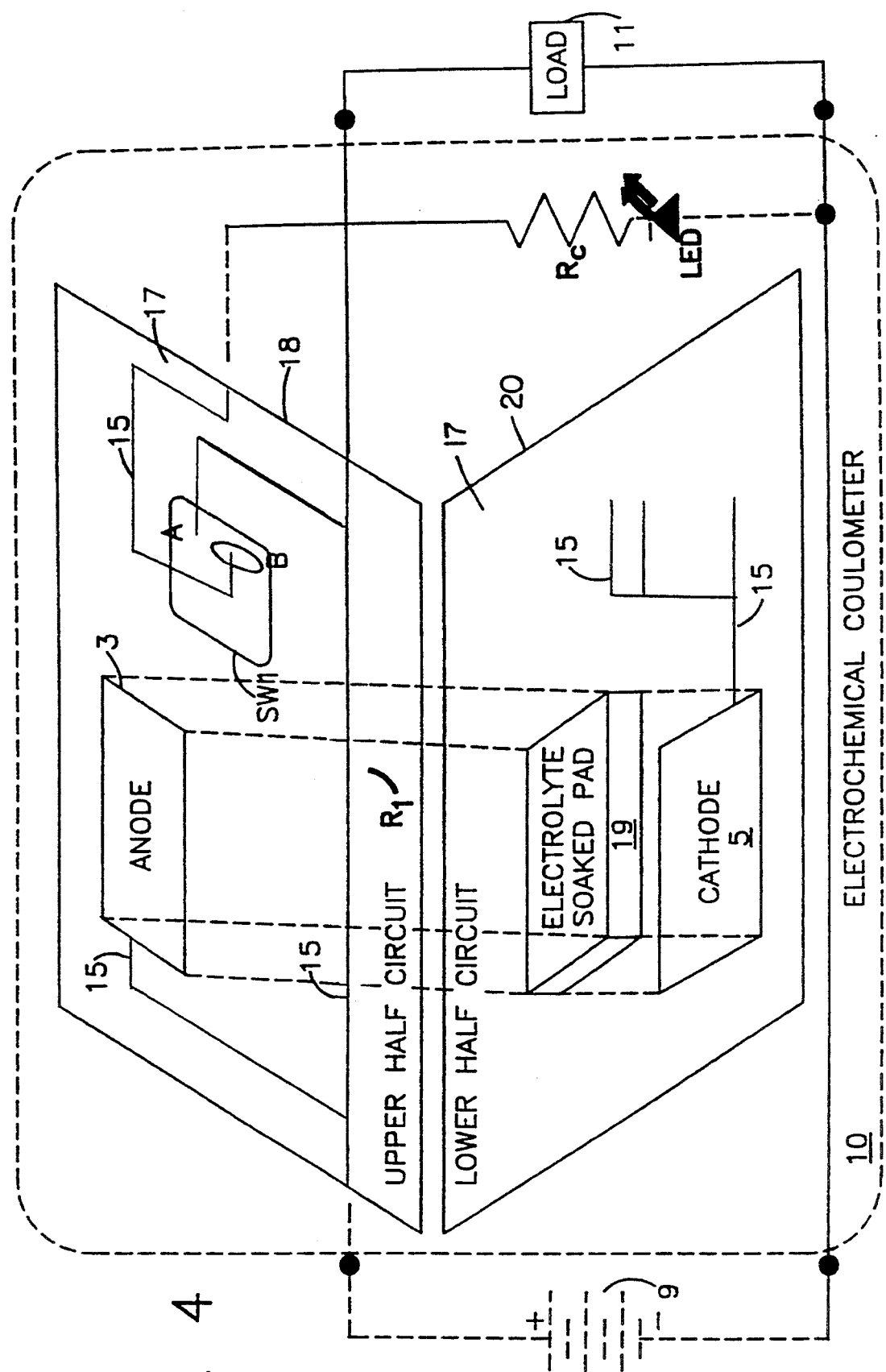
FIG. 4 shows a pictorial/circuit schematic and partial exploded assembly diagram of another embodiment of the invention.

This entire invention, with or without the measuring circuit, may be manufactured as discrete components or as pan of a single unit. One embodiment, as shown in FIG. 4, consists of metal strip-lines 15 such as copper electrolytically deposited on a non-conducting substrate 17 such as polyethylene, for example. $R_1$ is defined by the sheet resistance of the metal conductors or strips 15. The anode 3 and cathode 5 are of the same material such as copper, as the strip-lines 15 and of a surface area and thickness to produce the desired measure of charge as described above. An absorbent pad or separator 19 such as non-woven fabric saturated with solution such as copper sulfate in water separates the two electrodes 3 and 5 by a uniform fixed distance and provides the electrolyte 7, in this example. A press contact switch is used for SW1 to provide a measuring system such as that shown in FIG. 3. The two halves can be placed on the same or separate sheets and the sheet halves glued or sealed together.

In other embodiments of the invention, the current source may be any DC current source rather than a battery 9, such as a DC power supply, solar cell, charged capacitor, or compound electronic circuit. The resistor, $R_1$, may consist of a discrete resistor, strip-line resistor, variable resistor, electronic circuit which acts as a resistor, or a resistor in conjunction with a diode, capacitor, inductor, or electronic circuit. These other configurations of $R_1$ may allow variable settings for the relative current which flows through the electrochemical cell 1 versus the net current $i_{net}$, impedance matching, or the use of dissimilar electrode metals.

The electrochemical cell 1 consists of not less than two electrodes, the anode 3 and cathode 5, but may also include a third or reference electrode. The anode 3 and cathode 5 may consist of the same or dissimilar metals, metal oxides, or alloys, as above. Use of dissimilar metals will establish a cell potential and bias the voltage across the measuring device. In such an embodiment, $R_1$ may need a diode or other circuit included to limit reverse current, which would otherwise flow through $R_1$ as the electrochemical cell 1 acts as a battery. The electrodes need not be of the same metal as the conducting network connecting them.

The electrodes 3 and 5, for example, need not be of one metal layer. For example, the anode 3 may consist of more than one metal layer on top of another. As the first metal layer is stripped away, the second is exposed. The solution metal ions will be replaced with the second layer metal ions which will produce a different solution resistance which could indicate an intermediate charge limit has been reached.

The electrolytic solution 7 can be composed of a solvent or solvents and metal salt or salts. Solvents can be aqueous or non-aqueous. A supporting electrolyte such as TBAP (tetrabutylammonium perchlorate) or TEAP (tetraethylammonium perchlorate) may be added. The metal ions in solution 7 need not be the same as those composing the electrodes 3, 5. Consumption of one metal ion from solution and replacement with another will produce a change in solution resistance which could indicate an intermediate charge limit has been reached.

More than one electrochemical cell 1 can be placed in parallel with differing solution 7 concentrations. The resistances thereof will allow the majority of measuring current $i_2$ to pass through one cell 1 until consumed and the resistance of that cell will greatly increase. This could then be measured to indicate an intermediate charge limit has been reached. Multiple cells 1 would allow multiple limits.

The measuring device can be an integral component of the device or separate. Measurements can be continuous or on a test-as-desired basis. The LED meter system ($R_c$, 13) shown above is an example of an integral system which operates on a test as desired basis. An ohmmeter held across the electrochemical cell 1 when switch SW1 is open is an example of an external test-as-desired system. Measurements can be based on electrochemical cell 1 resistance, current $i_2$ through the electrochemical cell 1 when a fixed voltage is applied from a current source, or voltage across the electrochemical cell 1 when a current is applied. Detection may be made by a simple device such as an LED meter or liquid crystal sensing strip such as that used in inexpensive battery testers or a complex device or circuit. Addition of a reference electrode would permit connection to a circuit to measure the double layer potential at either the anode 3 or cathode 5 for use by a measuring circuit.

The device 10 or embodiments thereof can be connected to other circuits of a simple or complex nature to perform a further function. An example of such a circuit or device is a ground resistor which can be manually inserted in the circuit by the removal of an insulating tape should the test indicate a determined number of coulombs have passed. In the case of a battery, such as battery 9, this would allow the minor charge remaining in battery 9 to be drained or discharged making the battery environmentally acceptable before running out of power or becoming fully discharged during use. A battery 9 such as a lithium cell discharges into harmless metal salts.

Construction of a device incorporating an embodiment of the present invention can include all three major components as indicated above, or just the electrochemical cell 1. The required components can be constructed of separate or discrete parts or a single part can be separately connected, such as resistor $R_1$, or the electrochemical cell 1. This would allow adjustment of the current division or replacement of a consumed measuring cell 1. If the present device 10 is constructed as a single component, its basic structure can be made of any organic or inorganic non-conducting material or materials. The materials must be inert to the solvent used and allow for deposition and adhesion of a conducting surfaces or attachment of the separate components. Deposition of metal strip-lines 15 or electrodes 3, 5 could be accomplished by electrolyze deposition, printing, gluing, screening, vapor, plasma, or other vacuum deposition techniques, CVD, or LPE or other deposition techniques. Patterning can be accomplished before or after deposition of the metal. Adhesion of two or more components of the device can be accomplished by gluing, thermal joining, or other adhesion techniques. The solution pad 19 can be any organic or inorganic material not susceptible to damage by the electrolyte solution 7 but establishing a known distance between electrodes 3 and 5.

The distance between the electrodes 3 and 5 need not be uniform across the entire surface area thereof. The thickness of the electrodes 3 and 5 need not be uniform. The geometry of the electrodes 3 and 5 need not be squares in line with each other, but can be of any geometry oriented as desired with respect to the other. This will cause spatial variation in the consumption of the anode 3, which will in turn cause a continuous variation to the resistivity $R_2$ of the electrochemical cell 1.

Assuming a general configuration similar to that shown in FIG. 4, specific values for the variables can be obtained by making assumptions as indicated below:

Assume all metal strip-lines 15 and electrodes 3, 5 consist of copper.

Assume the metal strip-line 15 comprising $R_1$ is 1 cm wide, $10^{-3}$ cm thick, and 6 cm long.

Assume the electrolyte solution 7 is copper sulfate dissolved in water. The necessary concentration to produce the desired cell resistance $R_2$ will be determined below.

Assume the area of each of the electrodes 3 and 5 is 9 $cm^2$.

Assume the charge equivalent for the battery 9 reaction is "1" while the charge equivalent for the anode is "2".

Results of the calculations are to be made on a per mole of battery consumed basis rather than a specific number of moles.

Assume the desired ratio of current $i_2$ through the electrochemical cell 1 to the net current $i_{net}$ is 1:1000.

To establish maximum voltages experienced by the two parallel resistors $R_1$ and $R_2$, and the maximum power which must be dissipated in $R_1$, a maximum current output for the battery is assumed to be five amperes.

Substituting these values into the above equations yields the following results:

$R_1 = 1.034 \times 10^{-2} \Omega$
$R_2 = 10.33 \Omega$
$C^* = 7.25 \times 10^{-2}$ Normal
$t' = 3.562$ μm/mole of battery consumed
$V_{max} = 5.17 \times 10^{-2}$ volts
$P_{max} = 0.259$ watts These values demonstrate the reasonable parameters necessary to produce a working model of the measuring electrochemical coulometer 10.

Although various embodiments of the present invention have been shown and described hereon, they are not meant to be limiting. Those of skill in the art may recognize modifications to these embodiments, which modifications are meant to be covered by the spirit and scope of the appended claims.

Figure 5:
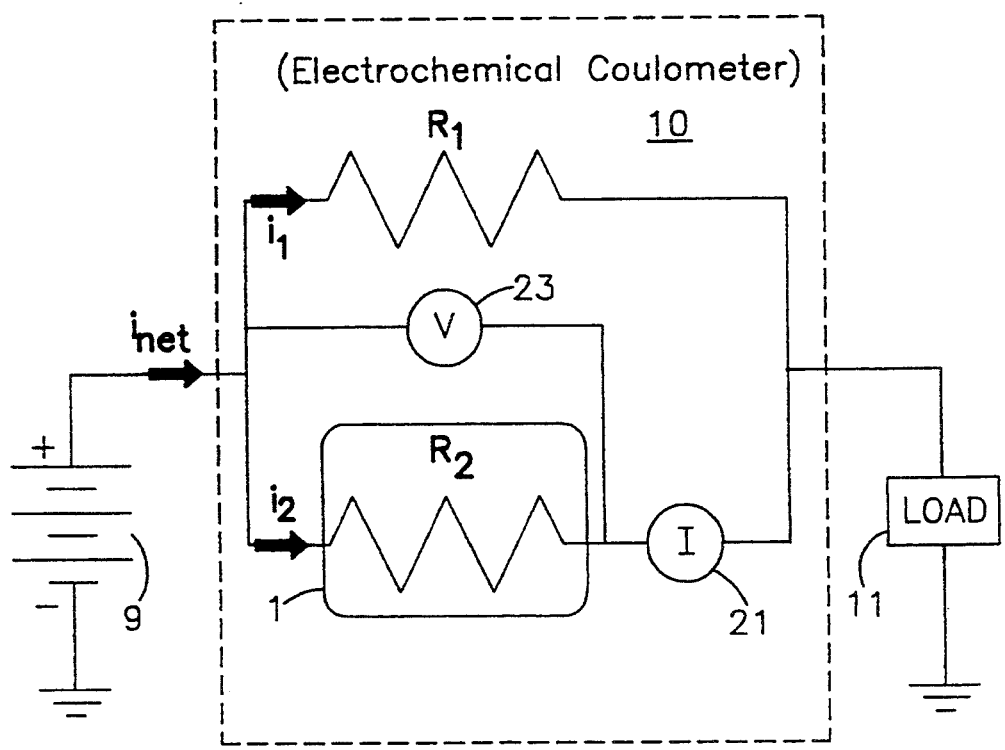
FIG. 5 is a simplistic circuit schematic diagram showing another embodiment of the invention.

For example, FIG. 5 shows a simple measuring circuit included in the embodiment of the invention of FIG. 1. The measuring circuit includes a voltmeter 23 connected across the electrochemical cell 1, and an ammeter 21 connected in series with electrochemical cell 1. Using Ohm's Law, by dividing the measured voltage V by the measured current I, the value of $R_2$ can be determined at any given time. As indicated above, changes in $R_2$ can be related to the accumulated time load 11 has been supplied current, or to the amount of charge removed from battery 9, and so forth.

In addition, as indicated above, the electrolyte can include a solvent that is either aqueous, non-aqueous, or a combination thereof. The solute can be other than copper sulphate. For example, the solute may also include any of perchlorates, nitrates, chlorides, fluorides, any metallic salt that will dissociate in the solvent to form an electrolyte solution, multiple salts, salts different than utilized electrode materials, and so forth.

The anode electrode 3 can be provided by any conductive material which will be consumed. The cathode electrode 5 can be provided by any conductive material capable of being deposited upon. Copper, gold, silver, metal oxides, and so forth, are examples of such conductive materials. The electrodes 3 and 5 can each consist of a substrate upon which one or more materials are formed.

In the embodiments of FIG. 4, the separator 19 can also be provided by a porous ceramic element, a gel of electrolyte, and so forth. It is important to note that separator 19 should be at least partially or wholly electrically insulative, ionically conductive, impervious to the solvent/solution of the electrolyte, and physically or geometrically stable.

What is claimed is:

1. An electric charge metering device comprising:
   an electrochemical cell for connection between a source of electric charge and a load, the electrochemical cell comprising an electrolyte sandwiched between a cathode and an anode, the electrochemical cell having a resistance of a predetermined value that changes in value as electric charge passes therethrough;
   a resistor of fixed value connected in parallel to the electrochemical cell, the resistor shunting a portion of the current flowing between said source and load away from said electrochemical cell;
   and means for measuring the difference in resistance between the electrochemcial cell and the resistor in real time;
   wherein the difference between the resistance of the electrochemical cell and the resistor provides a measure of the amount of current which has passed from the source to the load in real time.

2. The device of claim 1, wherein the anode and cathode of the electrochemical cell are metallic and whereby some metal ions in the electrolyte plate out by reduction at the cathode, and some of metal ions of the anode are consumed by oxidation in replenishing the electrolyte and at a predetermined time change the geometry/morphology of the anode, thereby causing the resistance between the charge passed therebetween.

3. The device of claim 2, wherein the electrochemical cell further includes:
   a separator of absorbent material soaked with the electrolyte, the separator being sandwiched between the anode and cathode electrodes.

4. The device of claim 1, wherein the measuring means includes:
   a voltmeter connected in parallel with the electrochemical cell for measuring the voltage V thereacross; and
   an ammeter connected in series with the electrochemical cell for measuring the current I flowing therethrough, whereby the resistance of the electrochemical cell equals V/I.

5. The device of claim 3, wherein the anode and cathode electrodes each include:
   a substrate of electrically non-conducting material; and a conductive material formed on a portion of one face of the substrate for providing the associated electrode.

6. The device of claim 4, wherein the anode and cathode electrodes each include:
   a substrate of electrically non-conducting material; and
   a conductive material formed on a portion of one face of the substrate for providing one of the anode and cathode electrodes.

7. The device of claim 3, wherein the metal includes copper, and the electrolyte consists of an aqueous copper sulfate solution.

8. The device of claim 7, further comprising:
   a first metal strip formed on the substrate carrying the anode electrode, for connecting the anode electrode for receiving current from a current source;
   a second metal strip formed on the substrate carrying the anode electrode, the second metal strip having one end connected to the first metal strip, and another end for connection to a load, the second metal strip providing a shunt resistance across the electrochemical cell; and
   a third metal strip formed on the substrate carrying the cathode electrode, the third metal strip having one end connected to the cathode electrode, and another end for connection to the load.

9. The device of claim 6, wherein the measuring means includes:
   a resistor;
   a light-emitting diode (LED meter) connected in series with the resistor; and
   switching means operable selectively connecting either the load or the series circuit of the LED meter and resistor between the cathode electrode and a return to a source of current, whereby when the LED meter is so switched into operation, the resulting light output of the LED meter is indicative of the resistance of the anode electrode being below a predetermined value.

10. A method for measuring state of electrical charge comprising the steps of:
    forming a metallic anode electrode on a first insulative substrate;
    forming a metallic cathode electrode on a second insulative substrate;
    providing an electrolytic solution between the anode and cathode electrodes;
    connecting one end of a current source to the anode electrode;
    connecting a load between the cathode electrode and the other end of the current source;
    measuring changes in the resistance of an electrochemical cell formed by the anode electrode, cathode electrode, and electrolyte in real time; and
    calculating either one or both of the total amount of charge taken from the current source between measuring intervals in real time or the amount of time current passed through the device between measuring intervals from the resistance changes and differences in the resistance across the electrochemical cell.

11. The method of claim 10, further including the step of connecting a resistor across the anode and cathode electrodes, for shunting all but a predetermined magnitude of current away from the current path formed by the anode and cathode electrodes, and electrolyte.

12. The method of claim 10, wherein the measuring step includes the steps of:
    measuring the magnitude of current flowing from the anode electrode, through the electrolyte, to the cathode electrode;
    measuring the voltage drop across the anode and cathode electrodes; and
    calculating the resistance of the electrochemical cell by dividing the measured voltage by the measured current.

13. An electrochemical device comprising:
    an anode electrode;
    a cathode electrode;

electrolyte means for applying an electrolyte at least between spaced apart ones of the anode and cathode electrodes;

a first terminal connected to the anode electrode for connection to one end of a source of current;

a second terminal connected to the cathode electrode for connection to one end of a load, the other end of the load being connected to the other end of the current source thereby permitting the device, a source of current, and a load to be connected into a series circuit; and means to measure the resistance of the device between the first and second terminals in real time which provide a measurable indicator of either one of the amount of charge taken from the current source between measuring intervals, or the amount of time current passed through the device between measuring intervals.

14. The electrochemical device of claim 13, wherein the electrolyte means includes:

a cell like housing for containing the electrolyte as an electrolytic solution; and the anode and cathode electrodes substantially immersed in the electrolytic solution.

15. The electrochemical device of claim 13, wherein the electrolyte means includes an absorbent structure of predetermined geometry filled with an electrolytic solution, and sandwiched between the anode and cathode electrodes.

16. The electrochemical device of claim 15, wherein the anode and cathode electrodes are each formed from copper adhered to an insulative substrate, and the electrolyte consists of an aqueous solution of copper sulphate.

17. The electrochemical device of claim 13, wherein the electrolyte means includes an aqueous electrolyte.

18. The electrochemical device of claim 13, wherein the electrolyte means includes a non-aqueous electrolyte.

19. The electrochemical device of claim 13, wherein the electrolyte means includes a combination of aqueous and non-aqueous electrolyte.

* * * * *